United States Patent [19]

Aine

[11] 4,058,725
[45] Nov. 15, 1977

[54] INFRARED ABSORPTION SPECTROMETER EMPLOYING A DUAL OPTOACOUSTIC DETECTOR

[76] Inventor: Harry E. Aine, 1804 Stierlin Road, Mountain View, Calif. 94040

[21] Appl. No.: 565,008

[22] Filed: Apr. 4, 1975

[51] Int. Cl.² .......................................... G01M 21/26
[52] U.S. Cl. ..................................... 250/343; 250/344
[58] Field of Search ............... 250/344, 343, 345, 346, 250/340, 339

[56] References Cited

U.S. PATENT DOCUMENTS

| 2,924,713 | 2/1960 | Liston | 250/344 |
| 3,215,832 | 11/1965 | Madsen | 250/344 |
| 3,447,876 | 6/1969 | Barringer | 250/344 |
| 3,659,941 | 5/1972 | Tong | 250/344 |
| 3,820,901 | 6/1974 | Kreuzer | 250/345 |
| 3,911,276 | 10/1975 | Bell | 250/343 |

OTHER PUBLICATIONS

"Absorption Coefficient Measurements of Nitrous Oxide and Methane at DF Laser Wavelengths," Deaton et al., Applied Phys. Letters, vol. 26, No. 6, 3/15/75.

Primary Examiner—Craig E. Church
Attorney, Agent, or Firm—Lowhurst & Aine

[57] ABSTRACT

An infrared laser absorption spectrometer is disclosed wherein a pair of detector cells are disposed in series relative to the laser beam path, such beam path preferably being within the optical cavity of the laser. The laser beam is modulated to produce a modulation of the absorption, if any, by the sample materials in the two cells. Modulated absorption by the sample or samples produces an acoustic wave in each cell which is detected by a suitable microphone and subtracted so as to produce a difference signal corresponding to the difference in absorption between the two cells so that undesired background effects are cancelled, such as window heating, absorption by a carrier gas or the like which is common to both cells. A mirror placed over one end of one of the cells allows a two cell optoacoustic detector geometry having only two windows therein. The dual optoacoustic cell is particularly useful for monitoring the output of a gas chromatograph since the background associated with the carrier stream can be cancelled.

22 Claims, 3 Drawing Figures

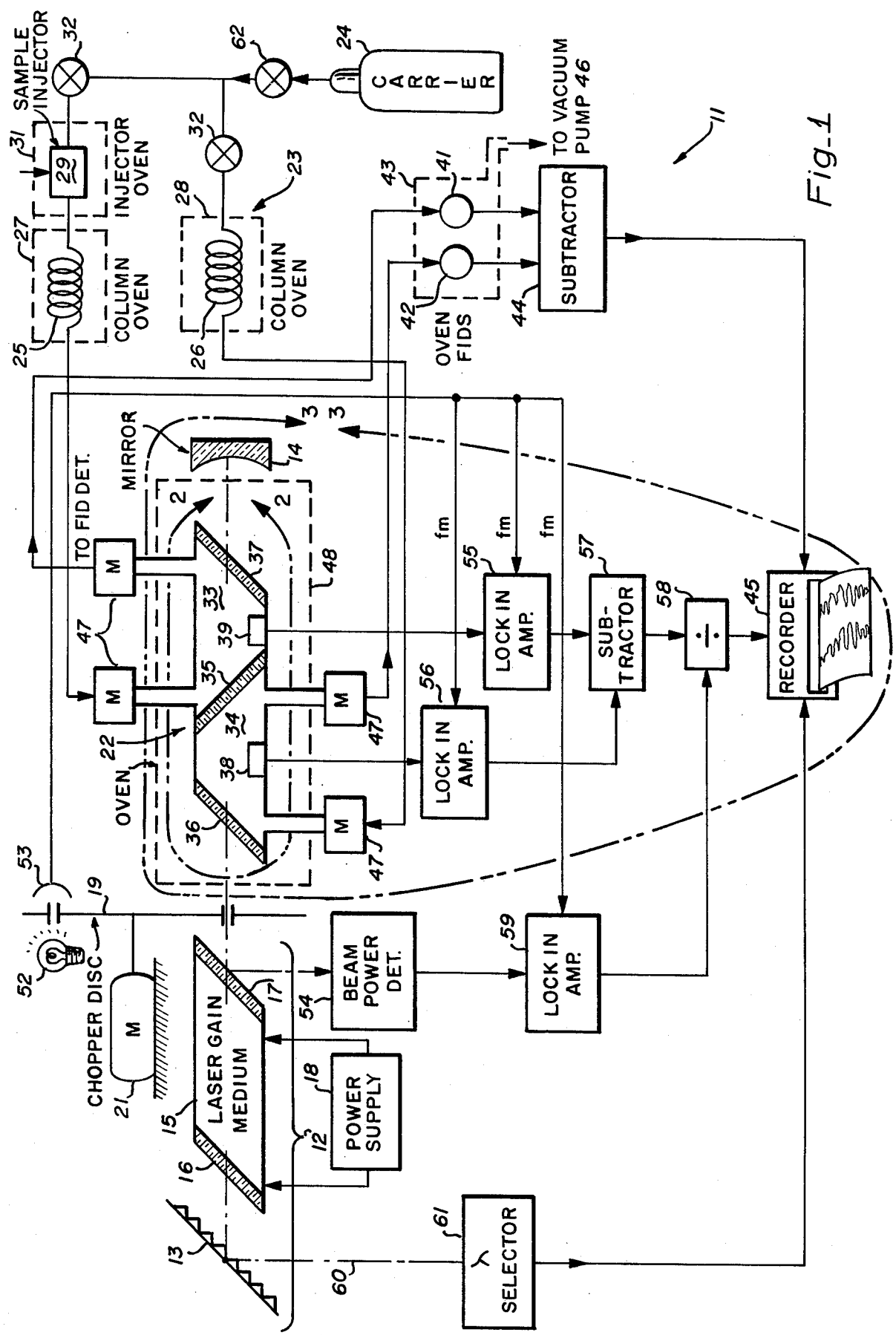
Fig._1

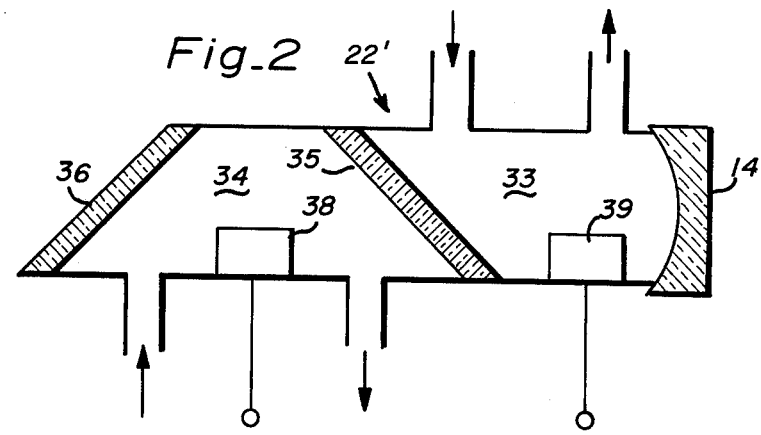
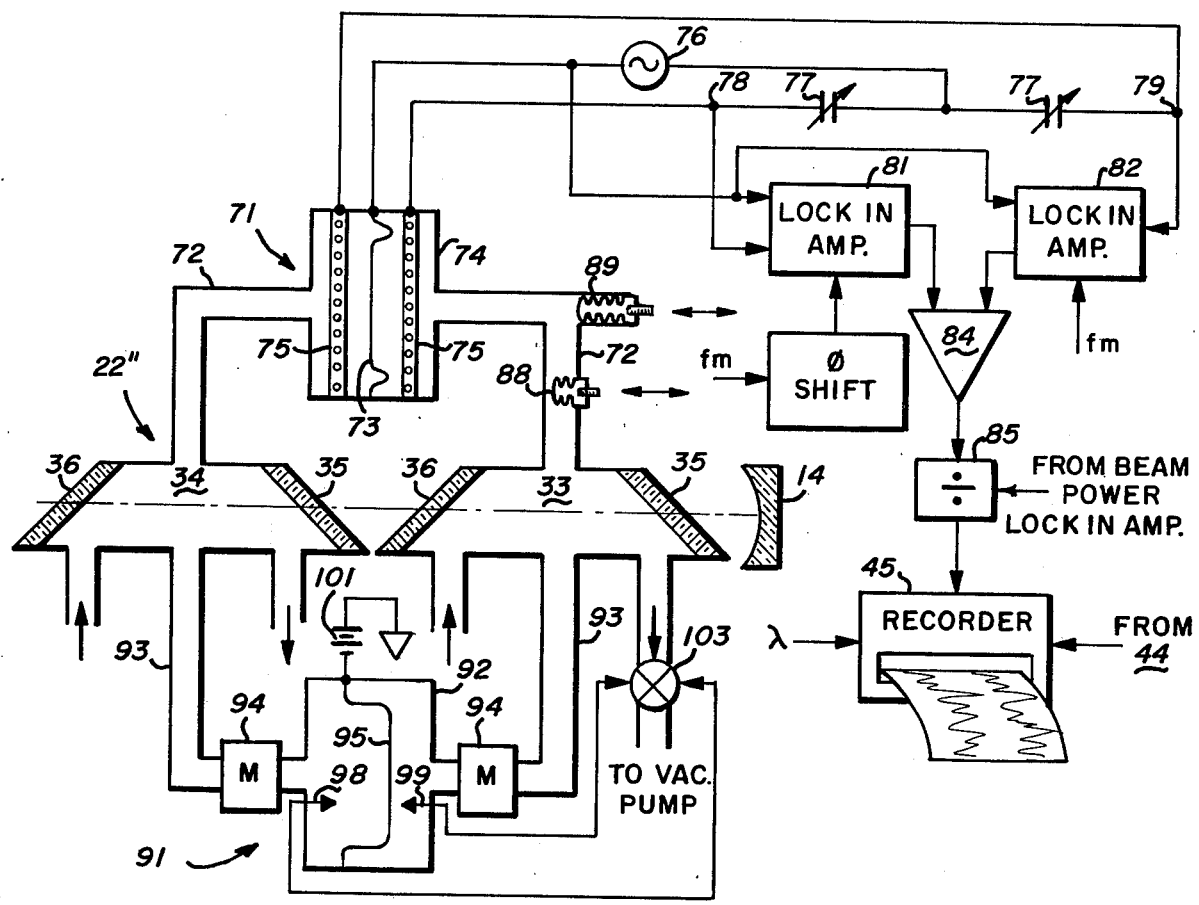

INFRARED ABSORPTION SPECTROMETER EMPLOYING A DUAL OPTOACOUSTIC DETECTOR

BACKGROUND OF THE INVENTION

The present invention relates in general to laser infrared absorption spectroscopy and more particularly to such spectroscopy employing an optoacoustic detector for detecting absorption of energy by the sample from the laser beam.

DESCRIPTION OF THE PRIOR ART

Heretofore, infrared laser absorption spectroscopy has employed an optoacoustic sample detection cell for analyzing gaseous samples and, in particular, for detecting certain pollutants in the air to concentration levels as low as parts per billion. Such a laser spectrometer is disclosed in: U.S. Pat. No. 3,820,901 issued June 28, 1974; in an article titled "Laser Optoacoustic Spectroscopy: A New Technique of Gas Analysis" appearing in *Analytical Chemistry*, Vol. 46, No. 2 of February 1947, pages 239–244; in *Science*, Vol. 177, pages 347–349 of July 28, 1972 in an article titled "Air Pollution: Sensitive Detection of Ten Pollutant Gases by Carbon Monoxide and Carbon Dioxide Lasers"; and in U.S. Pat. 3,659,452, issued May 2, 1972.

In these prior art laser absorption spectrometers, the laser, which is preferably a relatively high power output carbon dioxide or carbon monoxide laser, produces an output laser beam which is tunable to selected wavelengths within a band of infrared wavelengths of interest, i.e., the band of wavelengths over which certain gaseous sample constituents of interest are known to have infrared absorption spectra. The laser output beam is directed through an optoacoustic cell containing the gaseous material to be analyzed. A sensitive microphone is coupled to the gaseous sample inside the sample cell. The laser beam is chopped at a certain chopping frequency, as of 25 Hertz, to produce a corresponding modulation of the absorption, if any, of the laser beam energy by the sample gas under analysis. Absorption of energy from the laser beam by the gas produces heating thereof which results in generating an acoustic wave or quasi-static pressure field, at the chopping frequency, which is detected by the microphone. The detected signal is processed to produce an output signal as a function of the wavelength of the infrared energy of the tunable laser beam to derive an absorption spectrum of or absorption spectral data concerning the sample under analysis.

It is also known from the prior art to identify and resolve the retention time peaks of the effluent of a retention time chromatograph by feeding the effluent stream of the column through the optoacoustic detection cell of an infrared laser absorption spectrometer. Mufflers were provided for acoustically isolating the optoacoustic cell from the chromatographic column and from a flame ionization detector disposed downstream of the fluid passing through the optoacoustic cell. Such a combined IR laser absorption spectrometer and retention time chromatograph is disclosed in copending U.S. application Ser. No. 551,379, filed 20 Feb. 1975.

One of the problems encountered in an infrared laser absorption spectrometer is that undesired background signals are encountered. Some of these background signals are due to the heating of the windows of the optoacoustic cell. This problem is particularly pronounced when the modulation frequency of the laser beam is very low, i.e., in the order of 1 Hertz. In addition, the carrier gas which carries the sample material can have undesired absorption lines in the infrared spectrum which may produce interferring and spurious absorption lines in the spectrum of the material under analysis. Furthermore, if air is utilized as the carrier gas, contaminants in the air will appear as signals due to the absorption of the infrared radiation from the beam by the contaminants in the air. Also, many carrier gases are not sufficiently pure and their contaminants will introduce unwanted absorption lines superimposed on the spectrum of the sample under analysis.

Therefore, it is desired to obtain an improved infrared laser absorption spectrometer or detector method and apparatus in which the output signals can be made relatively free of unwanted background signals and noise.

It is also known from the prior art to dispose the optoacoustic cell of an infrared laser absorption spectrometer inside the optical cavity at the laser for increasing the power density of the laser beam within the optoacoustic cell. This substantially improves the sensitivity of the spectrometer for a given laser power and furthermore has several other significant advantages such as producing more laser lines of more nearly equal power. Such an infrared laser absorption spectrometer is disclosed and claimed in copending U.S. application Ser. No. 499,442 filed 22 Aug. 1974.

SUMMARY OF THE PRESENT INVENTION

The principal object of the present invention is the provision of an improved infrared laser absorption spectrometer of the type employing an optoacoustic detector.

In one feature of the present invention, a pair of optoacoustic detector cells are serially arranged along the beam path and the respective absorption signal outputs derived from the respective cells are subtracted one from the other to derive the difference to cancel certain undesired background signals and noise.

In another feature of the present invention, a mirror serves to close off one end of one of the optoacoustic detector cell of the dual cell geometry, whereby the number of infrared windows required in the system is reduced.

In another feature of the present invention the dual optoacoustic cell includes a common window partitioning the first cell from the second cell, whereby the number of windows required is reduced.

In another feature of the present invention, a common carrier substance is piped into the dual optoacoustic detector cells and a sample to be analyzed is injected or otherwise produced or introduced into only one of the cells, whereby the difference in the infrared absorption outputs of the two cells is indicative only of the absorption characteristics of the sample under analysis.

In another feature of the present invention a reference material is introduced into one of the cells of a dual optoacoustic detector cell and an unknown sample to be analyzed is introduced into the other cell and the difference in the absorption outputs of the two cells is indicative of the difference of the absorption characteristics of the sample to be analyzed relative to the reference material.

In another feature of the present invention, the same material can be introduced into both cells and an absorption determining parameter such as temperature, pressure, electrical field, magnetic field concentration, etc. of the sample in one cell varied relative to the other cell and the difference detected to derive information relative to the dependence of the absorption characteristic on the parameter being varied.

Other features and advantages of the present invention will become apparent upon a perusal of the following specification taken in connection with the accompanying drawings wherein:

BRIEF DESCRIPTION OF THE DRAWINGS

FIG. 1 is a schematic diagram, partly in block diagram form, of a combined infrared laser absorption spectrometer and retention time chromatograph incorporating features of the present invention.

FIG. 2 is an enlarged detailed view of an alternative embodiment of that portion of the structure of FIG. 1 delineated by line 2—2, and FIG. 3 is an alternative embodiment of that portion of the structure of FIG. 1 delineated by line 3—3.

DESCRIPTION OF THE PREFERRED EMBODIMENT

Referring now to FIG. 1, there is shown an infrared laser absorption spectrometer 11 incorporating features of the present invention. Briefly, the spectrometer 11 includes an optical cavity resonator 12 defined by the optical path between a diffraction grating 13 (wavelength selector) and a totally reflective mirror 14. A gas tight envelope 15, having Brewster angle windows 16 and 17 at opposite ends thereof, contains a conventional gaseous gain medium, such as carbon monoxide, carbon dioxide or a helium-neon mixture. The gain medium is interposed along the optical resonator path between the grating 13 and the mirror 14. The gain medium is excited by a suitable electrical discharge to provide coherent stimulated emission radiation at a resonant optical wavelength of the optical resonator 12. Power is supplied from a power source 18 to the gain medium to sustain the electrical discharge and the laser beam within the optical resonator 12 and inbetween opposite ends thereof.

The laser beam is modulated by means of a rotatable perforated chopper disc 19 driven by a motor 21. The speed of rotation of the chopper disc 19 and the spacing between the perforations in the disc 19 control the modulation frequency. In a typical example, the modulation frequency falls within the range of 10 to 400 Hertz.

A dual cell optoacoustic detector 22 is disposed in the beam path for interposing a sample medium, the infrared absorption of which is to be measured by the infrared laser absorption spectrometer 11, in the laser beam.

In the system of FIG. 1, the dual cells of the detector cells 22 are arranged for measuring the absorption of infrared radiation by the effluent of a gas chromatograph 23. The gas chromatograph 23 includes a source 24 of carrier gas, such as helium, which is piped via suitable conduit through a pair of essentially identical retention time chromatographic columns 25 and 26 each contained within its respective column oven 27 and 28 operating at the same temperature. A sample injector 29 is connected into one of the columns 25 upstream thereof for injecting a sample material to be analyzed into the carrier gas stream fed through column 25. The sample injector is contained within its own oven 31. Regulator valves 32 are provided for regulating the flow through each of the respective columns 25 and 26 so that the flow therethrough is essentially identical.

The chromatographic columns 25 and 26 serve to separate the various condensable constituents of the sample material in the fluid stream in accordance with their respective retention times for a specific packing material of the column and for the particular temperature of the column. Effluent streams from the respective columns 25 and 26 are fed to respective cell regions 33 and 34 of the dual cell detector 22. The cell regions 33 and 34 are serially spaced apart along the laser beam path inside the optical resonator 12. The cells are partitioned one from the other via the intermediary of a Brewster angle gas tight window 35. Opposite ends of the dual detector cell 22 are closed off via Brewster angle windows 36 and 37. Individual detector cell regions 33 and 34 are dimensioned to be substantially identical and each contains a respective microphone 39 and 38 coupled in acoustic wave energy exchanging relation with the fluid within the respective cell.

An output port is provided in each of the cell regions 33 and 34 for exhausting the sample gas from the cell and for feeding the exhausted gas to a respective flame ionization detector 41 and 42 of conventional design, each being contained within a common oven 43. Output signals from the flame ionization detectors are fed to a subtractor 44 for subtraction to derive a difference signal which is fed to one input of a recorder 45. Flame ionization detectors 41 and 42 are exhausted via an exhaust port to a vacuum pump 46. The vacuum pump is set to pump at such a rate as to preferably cause the flame ionization detectors 41 and 42, as well as the optoacoustic cells 33 and 34, to operate at subatmospheric pressure to prevent undue pressure line broadening of the infrared absorption lines of the sample constituents.

Mufflers 47 are coupled in line with both the input and output gas lines to the respective optoacoustic cells 33 and 34 to prevent coupling of unwanted noise into the optoacoustic cells and to prevent escape of the acoustic wave energy generated therein. The provision of mufflers in conjunction with the optoacoustic cell is disclosed and claimed in copending U.S. application Ser. No. 551,232, filed 20 Feb., 1975.

An oven 48 is disposed around the dual detector cell 22 for maintaining the detector cells 33 and 34 at a desired temperature to prevent undue temperature fluctuations of the dual detector cell in use. A light source 52 directs a beam of light through perforations of the disc 19 to a photodetector 53 as they come into alignment with the source 52 to produce an output corresponding to the modulation frequency of the laser beam. A beam power detector 54 is arranged to pick up a small amount of the beam power which is reflected from one of the Brewster angle windows 17 of the laser tube 15 to produce an output proportional to the beam power.

In operation, absorption of infrared radiation from the laser beam by sample constituents in the detector cells 33 and 34 produces a corresponding heating in each cell region 33 and 34 resulting in generation of an acoustic wave in each cell at the laser beam modulation frequency. These acoustic waves are picked up by respective microphones 39 and 38 and thence fed to respective inputs of lock-in amplifiers 55 and 56 wherein they are amplified against a reference at the beam modulation frequency derived from the photo detector 53. The respective outputs of the lock-in amplifiers 55 and 56 are fed to a subtractor 57 for subtraction therein to derive a difference signal which is then fed to one input of a divider 58. The output of the beam detector 54 is fed to one input of a lock-in amplifier 59 for detection and amplification against the beam modulation frequency reference derived from photo detector 53 to produce an output signal which is fed to the other input of the divider 58 for division into the difference absorption signal for normalization of the difference signal to the beam power.

The normalized difference signal is thence fed to the recorder 45 for recording as a function of retention time and as a function of the wavelength of the infrared laser beam energy. The wavelength is determined by a wavelength selector 61 which, via suitable mechanical linkage 60, changes the angle of the grating 13 to cause the laser to operate on certain predetermined operable wavelengths of the laser. This selected wavelength information is thus fed to the recorder 45 for recording as a function of retention time.

The advantage to the infrared laser optoacoustic spectrometer 11 of FIG. 1 is that contaminants in the carrier gas which are common to both cells produce absorption signals which cancel each other so that essentially only the absorption signal due to the sample material injected by the sample injector 29 appears in the difference output at the output of subtractor 57. Also, unwanted window heating effects similarly cancel. Furthermore, slight fluctuations in temperature and pressure of the system cancel.

As an alternative to using a purified source of carrier gas 24, the carrier gas supply 24 may be disconnected via valve 62 which is a three-way valve so that air may be admitted as the carrier. Although the air may have contaminants the absorption signals due to these contaminants will cancel in the dual cell geometry detector 22. Another advantage to use of the dual cells 33 and 34 in the optical resonator 12 is that, due to the multiple reflections of the wave energy between the end walls of the optical resonator, the beam power is equalized to identical values in both detector cells 33 and 34 regardless of the differences in adsorption of infrared wave energy from the beam by the sample in respective ones of the cells 33 and 34. In other words, since the laser beam passes through the cells 33 and 34 in both directions, within the optical resonator, the power is stabilized in the beam so that the beam power within each of the cells 33 and 34 is identical.

As an alternative to flowing the two samples through the two sample cell regions 33 and 34, such samples are simultaneously valved into and out of the cells at suitable intervals of time. Also, the dual detector cell geometry 22 permits a reference material to be disposed in one of the cells and an unknown material to be disposed in the other cell. When the absorptions are the same in both cells 33 and 34 at a number of wavelengths it is highly indicative that the unknown material corresponds to that of the known material in the reference cell portion of the detector 22. Also, since the output signal is a function of the concentration of the absorbing material and the respective cell, a known concentration of the material may be placed in the reference portion of the cell and the same material introduced into the second cell. By comparing the difference signal, the concentration of the material in the nonreference cell may be ascertained by scaling the difference signal derived at the output of divider 58. Furthermore, the dual cell geometry 22 may be used for detecting changes in absorption characteristics of a sample due to variation of an absorption determining parameter of the sample. For example, pressure, temperature, electric field, magnetic field, ionization, etc., can be varied in one cell relative to the other and the difference signal detected.

Referring now to FIG. 2 there is shown an alternative embodiment of the dual detector cell 22' wherein one end of the dual detector cell 22' is closed off by means of the mirror 14 instead of the Brewster angle window 37, thereby eliminating one of the windows and its associated loss in the optical resonator 12.

Referring now to FIG. 3 there is shown a preferred embodiment of that portion of the apparatus of FIG. 1 delineated by line 3—3. More particularly the structure of FIG. 3 depicts a preferred differential microphone structure and automatic pressure regulator for equalizing the pressure in the two cells 33 and 34. More particularly, each of the serially arranged cells 33 and 34 is made as identical as possible each having its respective input and output windows 36 and 35.

A differential microphone 71 is coupled to each of the cells 33 and 34 via identical tubulation 72 so that acoustic wave energy generated within each of the cells 33 and 34 by absorption of energy from the infrared beam is conducted through the tubulations 72 to opposite sides of the microphone diaphragm 73 which is sealed in a gas tight manner across a cylindrical chamber 72 in electrically insulative relation relative to the walls of the chamber 74.

A pair of perforated capacitor plates 75 are likewise sealed across the cylindrical chamber 72 in axially spaced relation from the diaphragm 72 on opposite sides thereof and preferably equally spaced from the diaphragm in close relation thereto. The perforated capacitive plates 75 are likewise sealed into the chamber 72 in electrically insulative relation with respect thereto and with respect to each other and to the microphone diaphragm 73.

A radio frequency generator 76 has one output thereof coupled to the diaphragm 73 and the other output coupled to respective capacitive plates 75 via load capacitors 77. The perforations in the capacitor plates 74 are dimensioned so as to provide a very low impedance to acoustic wave energy at the beam modulation frequency $f_m$ so that acoustic wave energy is coupled from each of the cells 33 and 34 via the tubulation 72 directly to opposite sides of the capacitive diaphragm 73.

When the acoustic wave pressure is higher in one of the cells relative to the other it will cause a deflection of the microphone diaphragm 73 toward the capacitor plate connected to the cell having the lower acoustic wave pressure, thereby producing an unbalance in the rf voltage at node 78 relative to that at node 79. The rf signals on nodes 78 and 79 are fed into respective lock-in amplifiers 81 and 82 for lock-in amplification first against a reference signal derived from the source 76 to demodulate the carrier and then lock-in amplification and detection against a sample of the laser beam modulation frequency $f_m$ applied to the other input of the respective lock-in amplifiers 81 and 82. The phase of one of the beam modulation frequency components fed into one of the lock-in amplifiers 81 or 82 is variable by phase shifter 83 as required to compensate for slight phase shifts encountered in the acoustic wave energy passing through the conduits 72 to the differential microphone 71.

The outputs of the lock-in amplifiers are fed to a differential amplifier 84 to derive a difference signal corresponding to the difference in the pressure within the chambers 33 and 34. This difference signal is thence fed to a divider 85 for dividing by a signal derived from the beam power lock-in amplifier 59 to derive a normalized difference absorption signal which is fed to the recorder 45 for recording as a function of retention time, wavelength of the infrared radiation, and the difference in the flame ionization detector outputs.

Load capacitors 77 are individually variable to compensate for slight physical displacements of the microphone diaphragm 73 relative to the respective capacitor plates 75. In operation, a pure carrier gas is fed into both cells 33 and 34 and the load capacitors 77 and phase shifter 83 are adjusted to produce a null of the difference signal at the output of differential amplifier 84. The sample material to be analyzed is fed, as by injection, into the carrier stream fed into one of the sample cells relative to the other to produce a difference signal corresponding only to absorption characteristics of the sample under analysis.

As an alternative to adjustment of the phase shifter 83, an adjustable impedance to pressure transmission, such as a bellows 88, is provided in one of the tubulations 72 to equalize the impedance of pressure transmission through both of the tubulations 72 to the differential microphone for the acoustic wave energy. The volume of the acoustic wave passages to the differential microphone 71 is trimmed via adjustable bellows 89 which adjust the volume of one of the tubulations to be equal to that of the other. In this manner the phase shifts for the acoustic wave energy can be adjusted so that they are equal through both of the passages 72 to the differential microphone 71.

An automatic pressure regulator for maintaining the pressure equal in both of the sample chambers 33 and 34 is shown at 91. The pressure regulator includes an enlarged cylindrical chamber 92 coupled in gas communication with each of the cells 33 and 34 via tubulations 93. Acoustic isolators or mufflers 94 are provided in each of the tubulations 93 for acoustically isolating the chamber 92 from the respective cells 33 and 34 at the laser beam modulation frequency $f_m$ without substantially isolating the chamber 92 from the sample chambers 33 and 34 at frequencies substantially below the beam modulation frequency. A thin flexible gas impervious diaphragm 95 is sealed across the chamber 92 in a gas tight manner at the periphery thereof for partitioning the chamber 92 into a pair of regions in gas communication with each of the cells 33 and 34. The compliance of pressure diaphragm 95 is made substantially greater than the compliance of the microphone diaphragm 73 so that the pressure diaphragm 95 will move in the required direction as necessary to equalize the pressure in both of the cells 33 and 34 without causing deflection of the microphone diaphragm 73.

Since the infrared absorption lines of most of the sample constituents are pressure sensitive, the automatic pressure regulator 95 serves to reduce unwanted background signals due to pressure differences in each of the respective sample cells 33 and 34. The mufflers 94 serve the purpose of perventing a short circuit of acoustic wave energy from one cell into the other.

Since the diaphragm 95 is operative only between its extremes of travel, a pair of electrical switches 98 and 99 are provided for sensing each extreme of travel of the diaphragm 95 by closing a circuit to the diaphragm 95 which is made conductive and biased by a voltage source 101. A sensed extreme signal is fed to control a restriction 102 in one of the exhausts of one of the cells 33 to increase the value of the restriction when switch 99 is actuated and to reduce the restriction when switch 98 is actuated.

The advantage of the differential microphone 71 as contrasted with the use of separate microphones in each of the sample chamber cells 33 and 34 is that only one microphone structure is utilized such structure being common to both the cells 33 and 34 to facilitate balancing of the microphone and eliminating the requirement for a second microphone.

RELATED CASES

The automatic pressure regulator and differential microphone in combination with a dual optoacoustic detector cell structure is disclosed and claimed in copending application Ser. No. 572,013 filed 28 Apr., 1975.

What is claimed is:

1. In a method of laser absorption detection of spectroscopy of an unknown sample of interest the steps of:
    producing a laser beam of coherent infrared radiation;
    providing first and second sample regions partitioned from each other and spaced apart serially along the common beam path;
    interposing first and second samples in the respective first and second sample regions for absorbing coherent radiation from the laser beam and for converting the absorbed coherent radiation into a second form of energy, one of said samples being the unknown sample of interest for which the absorption from the laser beam is to be detected;
    coupling detector means in energy exchanging relation with respective ones of said first and second sample regions for detecting the second form of energy resulting from the absorption of energy, if any, from the coherent infrared beam by the respective first and second samples; and
    deriving an output corresponding to the difference between the detected second forms of energy derived from the respective first and second sample regions for detection of the absorption of the laser beam by the unknown sample of interest.

2. The method of claim 1 including the steps of:
    exciting an optical resonator with the coherent laser beam of infrared radiation to produce such beam within the optical resonator and including the step of, disposing said first and second sample regions within the infrared beam within said excited optical resonator.

3. The method of claim 2 including the step of exciting coherent stimulated emission of radiation from a laser gain medium within said optical resonator to provide the laser beam.

4. The method of claim 3 including the step of varying the wavelength of the coherent radiation of said laser beam.

5. The method of claim 3 including the step of modulating the intensity of said laser beam.

6. The method of claim 5 including the step of detecting the absorption of energy from said laser beam by first and second samples within said first and second sample regions as a function of the modulation of the intensity of said laser beam.

7. The method of claim 3 wherein the samples are gaseous and the step of detecting the absorption of energy includes, detecting the pressure wave energy generated by the absorption of infrared energy in the respective gaseous sample from the laser beam.

8. The method of claim 1 including the step of, causing an infrared absorption determining parameter of the sample in one of said sample regions to differ from that of the sample in the other sample region, whereby the derived difference output is a function of the difference in the infrared absorption characteristics of the different absorption determining parameter of the samples in said first and second sample regions.

9. The method of claim 1 including the steps of:
causing a common carrier fluid samle constituent to be disposed in both of said first and second sample regions so that the absorption of energy by the common carrier fluid constituents substantially cancels out in the derived difference output, and introducing or producing a second sample constituent concentration within one of said sample regions substantially different than its composition or concentration in the other sample region so that the derived difference output is a function of the absorption charcteristic of the second sample constituent.

10. The method of claim 1 including the step of, connecting both of said sample regions in gas communication with the earth's atmosphere, and causing or producing a different sample composition in one of said sample regions relative to the other so that the derived difference output is a function of the difference of the infrared absorption characteristics of the samples in the two sample regions.

11. The method of claim 1 including the step of feeding the effluent stream from first and second substantially identical retention time chromatographic columns into said first and second sample regions as the first and second samples, respectively, and injecting into one of said chromatographic columns the unknown sample material to be analyzed so that the retention peaks in the effluent stream from one of the chromatographic columns is different from that of the other so that the difference output is characteristic of the infrared absorption characteristics of the retention time peak of the unknown sample material in the effluent stream of the one chromatographic column.

12. The method of claim 2 including the step of controlling the pressure of said first and second samples within said first and second sample regions.

13. The method of claim 1 including the step of controlling the pressure of said first and second samples within said first and second sample regions.

14. In an infrared laser absorption detection of spectrographic apparatus for detecting absorption of laser energy by an unknown sample of interest:
means for producing a laser beam of coherent infrared radiation;
means for providing first and second sample regions partitioned from each other and spaced apart serially along the common beam path;
means for interposing first and second samples in the respective first and second sample regions for absorbing coherent radiation from the laser beam and for converting the absorbed coherent radiation into a second form of energy, one of said samples being the unknown sample of interest for which the absorption from the laser beam is to be detected;
detector means coupled in energy exchanging relation with respective ones of said first and second sample regions for detecting the second form of energy resulting from the absorption of energy, if any, from the coherent infrared beam by the respective first and second sample; and
means for deriving an output corresponding to the difference between the detected second form of energy derived from the respective first and second sample regions for detection of the absorption of the laser beam by the unknown sample of interest.

15. The apparatus of claim 14 including, optical resonator means excited with the laser beam of infrared radiation to produce such beam within said optical resonator, and wherein said first and second sample regions are disposed within the infrared beam within said optical resonator.

16. The apparatus of claim 15 wherein said means for producing a laser beam includes a laser gain medium disposed wtihin said optical resonator.

17. The apparatus of claim 15 wherein said means for providing said first and second sample regions includes, reflector means defining one end of said optical resonator means and one end wall of a structure defining one of said sample regions.

18. The apparatus of claim 14 wherein said means for providing said first and second sample regions includes, a hollow structure having said first and second sample regions therein for containing the samples, and infrared wave transmissive gas impermeable partitioning means disposed within said hollow structure for partitioning said first and second sample regions from each other with said partitioning means providing a common wall between said first and second sample regions.

19. The apparatus of claim 14 including means for causing an infrared absorption determining parameter of the sample in one of the said sample regions to differ from that of the sample in the other sample region, whereby the derived difference output is a function of the difference in the infrared absorption characteristics of the difference absorption determining parameter of the samples in said first and second sample regions.

20. The apparatus of claim 14 including first and second substantially identical retention time chromotographic columns, means for feeding the effluent streams from said first and second columns into said first and second sample regions as the firs t and second samples, respectively, and means for injecting into one of said chromatographic columns a sample material to be analyzed so that the retention peaks in the effluent stream from one of the chromatographic columns is different from that of the other so that the difference output is characteristic of the infrared absorption charateristics of the retention time peak of the sample material in the effluent stream of the one chromatographic column.

21. The apparatus of claim 14 including means for controlling the pressure of said first and second samples within said first and second sample regions.

22. The apparatus of claim 15 including means for controlling the pressure of said first and second samples within said first and second sample regions.

* * * * *